United States Patent
Oh et al.

(10) Patent No.: US 6,767,540 B2
(45) Date of Patent: Jul. 27, 2004

(54) USE OF ANTAGONISTS OF PLASMINOGEN ACTIVATOR INHIBITOR-1 (PAI-1) FOR THE TREATMENT OF ASTHMA AND CHRONIC OBSTRUCTIVE PULMONARY DISEASE

(75) Inventors: Chad K. Oh, North Rolling Hills Estates, CA (US); Seong H. Cho, Seoul (KR); Sossiena Demissie-Sanders, Houston, TX (US); David W. Thomas, Houston, TX (US); Sunny Tan, Missouri City, TX (US)

(73) Assignee: Tanox, Inc., Houston, TX (US)

( * ) Notice: Subject to any disclaimer, the term of this patent is extended or adjusted under 35 U.S.C. 154(b) by 0 days.

(21) Appl. No.: 09/759,999

(22) Filed: Jan. 12, 2001

(65) Prior Publication Data

US 2002/0086838 A1 Jul. 4, 2002

Related U.S. Application Data

(60) Provisional application No. 60/176,211, filed on Jan. 14, 2000.

(51) Int. Cl.[7] ............... A61K 39/395; A61K 39/00; C07K 16/00
(52) U.S. Cl. ............... 424/130.1; 424/134.1; 424/141.1; 424/146.1; 424/184.1; 530/387.1; 530/388.1; 530/388.2; 530/383.1; 530/389.2
(58) Field of Search ............... 424/130.1, 134.1, 424/141.1, 146.1, 184.1; 530/387.1, 388.1, 388.2, 389.1, 389.2

(56) References Cited

FOREIGN PATENT DOCUMENTS

WO  WO95/30438  * 6/1994

OTHER PUBLICATIONS

Cho et al. (J of Immunol. 2000, 165, 3154–3161).*

Banach–Wawrzenczyk, E., et al. [No title available]. *Pol Merkuriusz Lek.* 2000. Jan.; 7(43):9–11[English abstract only].

Dziedziczko, A., et al. Changes in platelet function, activated partial thromboplastin time and plasminogen activator inhibitor in patients with bronchial asthma after prednisone treatment. *Pneumonol Alergol Pol.* 1998. 66(3–4):173–7 [English abstract only].

Olman, Mitchell A. et al. Changes in Procoagulant and Fibrinolytic Gene Expression during Bleomycin–induced Lung Injury in the Mouse. *Journal of Clinical Investigation* Sep. 1995. vol. 96. 1621–1630.

Cho, Seong H., et al. Production of Plasminogen Activator Inhibitor–1 by Human Mast Cells and Its Possible Role in Asthma. *The Journal of Immunology.* 2000. 165: 3154–3161.

Eitzman, D. T. et al., "Bleomycin–Induced Pulmonary Fibrosis in Transgenic Mice That Either Lack or Over express the Murine Plasminogen Activator Inhibitor–1 Gene", *J. Clin. Invest.* 1996, 97:232–237.

* cited by examiner

*Primary Examiner*—Christina Chan
*Assistant Examiner*—Michail A Belyavskyi
(74) *Attorney, Agent, or Firm*—Cheryl A. Liljestrand

(57) ABSTRACT

The invention relates to methods for treatment of asthma and chronic obstructive pulmonary disease (COPD) by administration of antagonists to plasminogen activator inhibitor type-1 (PAI-1). Suitable atagonists include antibodies, peptides, proteins, nucleic acids, small organic molecules and polymers.

12 Claims, No Drawings

SEQUENCE LISTING

```
<160> NUMBER OF SEQ ID NOS: 8

<210> SEQ ID NO 1
<211> LENGTH: 18
<212> TYPE: DNA
<213> ORGANISM: Artificial Sequence
<220> FEATURE:
<223> OTHER INFORMATION: murine PAI-1 primer

<400> SEQUENCE: 1
agcagagtgg agggcaca                                                 18

<210> SEQ ID NO 2
<211> LENGTH: 18
<212> TYPE: DNA
<213> ORGANISM: Artificial Sequence
<220> FEATURE:
<223> OTHER INFORMATION: murine PAI-1 primer

<400> SEQUENCE: 2
gatgccgtat gccacggt                                                 18

<210> SEQ ID NO 3
<211> LENGTH: 21
<212> TYPE: DNA
<213> ORGANISM: Artificial Sequence
<220> FEATURE:
<223> OTHER INFORMATION: murine GAPDH primer

<400> SEQUENCE: 3
gagtctactg gtgtcttcac c                                             21

<210> SEQ ID NO 4
<211> LENGTH: 22
<212> TYPE: DNA
<213> ORGANISM: Artificial Sequence
<220> FEATURE:
```

```
<223> OTHER INFORMATION: murine GAPDH primer

<400> SEQUENCE: 4
gtcatgagcc cttccacaat gc                                          22

<210> SEQ ID NO 5
<211> LENGTH: 17
<212> TYPE: DNA
<213> ORGANISM: Artificial Sequence
<220> FEATURE:
<223> OTHER INFORMATION: PAI 5G allele alternative forward primer

<400> SEQUENCE: 5
gtctggacac gtggggg                                                17

<210> SEQ ID NO 6
<211> LENGTH: 17
<212> TYPE: DNA
<213> ORGANISM: Artificial Sequence
<220> FEATURE:
<223> OTHER INFORMATION: PAI 4G allele alternative forward primer

<400> SEQUENCE: 6
gtctggacac gtgggga                                                17

<210> SEQ ID NO 7
<211> LENGTH: 20
<212> TYPE: DNA
<213> ORGANISM: Artificial Sequence
<220> FEATURE:
<223> OTHER INFORMATION: PAI reverse primer

<400> SEQUENCE: 7
gctgtccacc cggtgctctg                                             20

<210> SEQ ID NO 8
<211> LENGTH: 26
<212> TYPE: DNA
<213> ORGANISM: Artificial Sequence
<220> FEATURE:
<223> OTHER INFORMATION: Control reverse primer

<400> SEQUENCE: 8
aagcttttac catggtaacc cctggt                                      26
```

USE OF ANTAGONISTS OF PLASMINOGEN ACTIVATOR INHIBITOR-1 (PAI-1) FOR THE TREATMENT OF ASTHMA AND CHRONIC OBSTRUCTIVE PULMONARY DISEASE

This application claims the benefit of U.S. Provisional Application No. 60/176,211, filed on Jan. 14, 2000.

BACKGROUND OF THE INVENTION

The mechanisms responsible for the development of asthma in atopic patients include genetic predisposition and the effects of environmental exposures to inflammatory stimuli in the airways of susceptible individuals (Bleecker, E. R., and D. A. Meyers in *Genetics of Allergy and Asthma*. M. N. Blumenthal, and B. Bjorksten, (eds. Marcel Dekker, New York, p. 307 1997). Asthma represents a chronic inflammatory process of the airways. The consequences of chronic inflammation in the asthmatic airways include increased numbers of fibroblasts and the deposition of extracellular matrix (ECM) such as collagen, fibronectin, and laminin within the airway wall (Altraja, A., et al. *Am. J. Respir. Cell. Mol. Biol.* 15: 482, 1996; Roche, W. R., et al. *Lancet.* 1:520, 1989). The plasminogen activator (PA) system has an important role in controlling endogenous fibrosis and regulating ECM proteolysis relevant to tissue remodeling (Gabazza, E. C., et al. *Lung*. 177: 253, 1999). The tissue-type PA (tPA) and urokinase-type PA (uPA) converts plasminogen to plasmin, which enhances proteolytic degradation of the ECM. An important mechanism in the regulation of PA activity is inhibition of uPA or tPA by three major inhibitors, which are PAI-1, PAI-2, and PAI-3 (Kruitoff, E. K. *Enzyme* 40: 113, 1988). Among these three inhibitors, PAI-1 is the most important in controlling lung fibrosis (Geiger, M., et al, *Immunopharmacology* 32: 53, 1996; Lardot, C., et al. *Eur. Respir. J.* 11: 912, 1988; Kruitoff E. K., et al. *J. Biol. Chem.* 261: 11207, 1986). PAI-1 overexpressing mice suffered severe lung injury and deposition of ECM after bleomycin challenge (Eitzman, D. T., et al. *J. Clin. Invest.* 97: 232, 1996) or hyperoxia (Barazzone, C., et al. *J. Clin. Invest.* 98: 2666, 1996), whereas PAI-1 deficient mice were protected against such a fibrotic reaction. These findings show that PAI-1 is closely associated with fibrosis and ECM accumulation after lung injury or inflammation. Recently, the induction of PAI-1 was demonstrated in mast cells of the asthmatic airway (Cho, S. H., et al. *J. Immunol.* 165: 3154–3161, 2000).

The human PAI-1 gene is located on chromosome 7 (q21.3–q22) and contains eight introns and nine exons distributed over about 12.3 kb (Klinger, K. W., et al. *Proc. Natl. Acad. Sci. U.S.A.* 84: 8548, 1987). Eight polymorphisms of the PAI-1 gene have been discovered up to now, but only a few genotypes seem to influence the synthesis and both concentration and activity of the inhibitor in plasma (Dawson, S. J., et al. *J. Biol. Chem.* 268: 10739, 1993; Hermans, P. W., et al. *Lancet.* 354: 556, 1999; Dawson, S., et al. *Arteriosclero. Thromb.* 11: 183, 1991; Mansfield, M. et al. *Thromb. Haemost.* 71: 731, 1994). The most important of these is a single guanosine insertion/deletion variation (5G or 4G) in the promoter region (4G deletion polymorphism), situated 675 bp upstream from the transcriptional start site of the PAI-1 gene (Dawson, S. J., et al. *J. Biol Chem.* 268: 10739, 1993; Eriksson, P., et al,. *Proc. Natl. Acad. Sci USA* 92: 1851, 1995). The 4G allele is correlated with increased plasma PAI-1 levels. In vitro experiments have initially shown that the 5G allele contains an additional binding site for a protein likely related to the NF-κB group of transcription factors, and this binding site is absent in the 4G allele (Dawson, S. J., et al. *J. Biol. Chem.* 268: 10739, 1993). After stimulation with IL-1, HepG2 cells transfected with the 4G allele produce six times more PAI-1 mRNA than those with the 5G allele. These data suggest a functional role of the 4G/5G polymorphism in response to cytokines, the 4G allele being associated with enhanced gene expression (Dawson, S. J., et al. *J. Biol. Chem.* 268: 10739, 1993). Both alleles bind a transcriptional activator, whereas the 5G allele also binds a repressor protein to an overlapping binding site, which decreases the binding of the activator by interference due to steric hindrance. A relationship between increased PAI-1 levels in plasma and the 4G polymorphism has been described in patients with cardiovascular and metabolic diseases (Dawson, S. J., et al. *J. Biol. Chem.* 268: 10739, 1993; 16–20).

Treatment of bronchial asthma patients with prednisone resulted in an increase of PAI-1 activity (Banach-Wawrzenczyk, E. et al., *Pol. Merkuriusz Lek* 7(43): 9–11, 2000; Dziedzicko, A. et al., *Pneumonol. Alergol Pol* 66(3–4): 173–177, 1998). No statistical difference were found with other fibrinolysis factors after the treatment.

Bleomycin-induced lung injury was reported to result in increased PAI-1 activity levels (Olman, M. A. et al. *J. Clin. Invest.* 96(3): 1621–1630, 1995). In situ hybridization showed mRNA induction. The observations suggested that PAI-1 expression plays an important role in the formation and persistence of extracellular fibrin in injured lung tissue.

There exists a need for asthma treatments and chronic obstructive pulmonary disease treatments. These treatments may be able to take advantage of the observed PAI-1 activity levels.

SUMMARY OF THE INVENTION

Antagonists to plasminogen activator inhibitor type-1 (PAI-1) can be used for the treatment of asthma and chronic obstructive pulmonary disease (COPD). Antagonists can be antibodies, peptides, proteins, nucleic acids, small organic molecules, or polymers.

DESCRIPTION OF THE SEQUENCE LISTINGS

The following sequence listings form part of the present specification and are include to further demonstrate certain aspects of the present invention. The invention may be better understood by reference to one or more of these sequences in combination with the detailed description of specific embodiments presented herein.

| SEQ ID NO: | Description | Sequence |
|---|---|---|
| 1 | Murine PAI-1 sense | AGCAGAGTGGAGGGCACA |
| 2 | Murine PAI-1 antisense | GATGCCGTATGCCACGGT |
| 3 | Murine GAPDH sense | GAGTCTACTGGTGTCTTCACC |
| 4 | Murine GAPDH antisense | GTCATGAGCCCTTCCACAATGC |
| 5 | 5G alternative forward primer | GTCTGGACACGTGGGGG |
| 6 | 4G alternative forward primer | GTCTGGAGACGTGGGGA |
| 7 | Reverse primer | GCTGTCCACCCGGTGCTCTG |
| 8 | Control reverse upstream primer | AAGCTTTTACCATGGTAACCCCTGGT |

DEFINITIONS

The following definitions are provided in order to aid those skilled in the art in understanding the detailed description of the present invention.

"Antibodies" refers to whole antibodies and antibody fragments or molecules including antibody fragments, including, but not limited to, single chain antibodies, humanized antibodies, DEIMMUNISED™ antibodies, and Fab, F(ab')$_2$, V$_H$, V$_L$, F$_d$, and single or double chain Fv fragments.

"PAI" refers to plasminogen activator inhibitor; "PAI-1" refers to plasminogen activator inhibitor type-1.

"TDT" refers to transmission disequilibrium test.

"ECM" refers to extracellular matrix.

"tPA" refers to tissue-type plasminogen activator.

"uPA" refers to urokinase-type plasminogen activator.

"FITC" refers to fluorescein-isothiocyanate.

DETAILED DESCRIPTION OF THE INVENTION

PAI-1 is shown to be highly expressed in the airways of a murine asthma model. Additionally, the 4G allele was shown to be preferentially transmitted to asthmatic children. These results suggest a possible role of PAI-1 gene and the 4G polymorphism in the pathophysiology of asthma. Antagonists of PAI-1 can be used to reduce or eliminate asthma or chronic obstructive pulmonary disease.

The induction of the PAI-1 gene in the lung tissue of a murine asthma model was shown using both a RT-PCR and an immunofluorescence approach. Although many cell types are capable of synthesizing PAI-1 (Loskutoff, D. J., M. Sawdey, and J. Mimuro. *Prog. Hemost. Thromb.* 9: 87, 1995), endothelial cells may be the major source of PAI-1 under basal conditions (Yamamoto, C., et al. *Thromb. Res.* 74: 163, 1994). Prinsky et al. demonstrated that macrophages appeared to be the principal cell type secreting PAI-1 in lung tissue under hypoxic conditions (*J. Clin. Invest.* 102: 919, 1998). Mast cells have been shown to be one of the important sources of PAI-1 in the asthmatic airways (Cho, S. H., et al. *J. Immunol.* 165: 3154, 2000). Taken together, the main sources of increased PAI-1 levels in the lung tissue of this murine asthma model appear to be endothelial cells, macrophages, and mast cells. PAI-1 secretion was shown to be increased in the airways of the murine asthma model, suggesting that PAI-1 secretion may also be increased in the asthmatic airways. These results are consistent with the report demonstrating that the levels of PAI-1 in the BAL fluids were increased in patients with idiopathic pulmonary fibrosis (Kotani, I., et al. *Thromb Res.* 77: 493, 1995).

In order to investigate the potential contribution of polymorphism with the PAI-1 gene to the development of asthma nuclear families were recruited from Nottingham UK on the basis of affected sib-pairs for asthma. Using a TDT approach, preferential transmission of the 4G allele to asthmatic children was demonstrated. The trend towards increased transmission of the 4G allele was also seen with the phenotype atopy, but the number of informative families was smaller due to the high prevalence of atopy within these families and no significant effect was observed. The prevalence of the 4G allele in the Nottingham families is slightly higher than that reported in a previous UK study on healthy individuals (Hermans, P. W., et al. *Lancet.* 354: 556, 1999) and the prevalence of the 4G allele was also higher than that reported in previous population based studies in caucasian populations (Eriksson, P., B. et al. *Proc. Natl. Acad. Sci USA* 92: 1851, 1995; Westendorp, R. G., et al. *Lancet.* 354: 561, 1999). This could be explained either by differing prevalence of the 4G allele in different caucasian populations or by the possibility that individuals carrying the 4G allele may have been preferentially included in this study because of an association of the allele with asthma. The demonstration of increased transmission of the 4G allele in asthmatic siblings is in keeping with the observed functional effects of this allele in vitro (Dawson, S. J., et al. *J. Biol. Chem.* 268: 10739, 1993), with increased levels of PAI-1 in the plasma of individuals carrying this allele due to increased transcriptional activity of the gene. One would also predict that in addition to potentially contributing to the development of asthma per se, this polymorphism might be important in determining the severity of the disease and could contribute to the development of bronchial hyperresponsiveness.

These results suggests that the gene for PAI-1 may predispose to the development of asthma and contribute to the airway remodeling seen in a model of chronic asthma. Inhibitors of PAI-1 (Eitzman, D. T., et al. *J. Clin. Invest.* 95: 2416, 1995) can inhibit the development of asthma or alter the chronic airway remodeling which occurs in the disease.

Antagonists to PAI-1 can be used in the treatment of asthma and chronic obstructive pulmonary disease. Antagonists can be antibodies, peptides, proteins, nucleic acids, small organic molecules, or polymers. Preferably, the antagonist is an antibody. Antagonists may be prepared as a composition with a pharmaceutically acceptable carrier or diluent. Carriers and diluents refer to any and all solvents, dispersion media, antibacterial agents, antifungal agents, microcapsules, liposomes, cationic lipid carriers, isotonic and absorption delaying agents and the like which are not incompatible with the antagonist.

The antibody can be a monoclonal or polyclonal antibody. The antibody can be chemically linked to another organic or bio-molecule. Monoclonal and polyclonal antibodies may be made by any method generally known to those of skill in the art. U.S. Pat. No. 5,422,245 (issued Jun. 6, 1995) describes the production of monoclonal antibodies to plasminogen activator inhibitor.

Peptides, proteins, nucleic acids, small organic molecules, and polymers may be identified by combinatorial methods.

Known PAI-1 antagonists may be used, for example spironolactone, imidapril, angiotensin converting enzyme inhibitors (ACEI, captopril, or enalapril), angiotensin II receptor antagonist (AIIRA), or defibrotide (a polydeoxyribonucleotide).

PAI-1 antisense nucleic acid molecules may be used to reduce the levels of PAI-1 in treating asthma or chronic obstructive pulmonary disease.

An embodiment of the invention is directed towards a method to treat asthma in a mammal. The method preferably comprises selecting a mammal diagnosed with asthma, and administering to the mammal a plasminogen activator inhibitor-1 antagonist. The antagonist is preferably administered at a concentration suitable to reduce the effects of asthma. The concentration of the antagonist is preferably less than about 100 $\mu$M, about 10 $\mu$M, about 1 $\mu$M, about 0.1 $\mu$M, about 0.01 $\mu$M, about 0.001 $\mu$M or about 0.0001 $\mu$M. The administering step can be performed by any acceptable means, including oral, inhalation, topical, IV, IP, and IM administration. The mammal can generally be any mammal susceptible to asthma, preferably is a human, a cat, a dog, a cow, a horse, a pig, or a goat, and more preferably is a human. The plasminogen activator inhibitor-1 antagonist can generally be any plasminogen activator inhibitor-1 antagonist. Preferably, the plasminogen activator inhibitor-1 antagonist is an antibody, a protein, a peptide, a polynucleotide, or a small organic molecule. The antibody can be a monoclonal antibody or a polyclonal antibody. The plasminogen activator inhibitor-1 antagonist can be spironolactone, imidapril, an angiotensin converting enzyme inhibitor, captopril, enalapril, an angiotensin II receptor antagonist, or defibrotide.

An additional embodiment of the invention is directed towards a method to treat chronic obstructive pulmonary disease in a mammal. The method preferably comprises selecting a mammal diagnosed with chronic obstructive pulmonary disease, and administering to the mammal a plasminogen activator inhibitor-1 antagonist. The antagonist is preferably administered at a concentration suitable to reduce the effects of chronic obstructive pulmonary disease. The concentration of the antagonist is preferably less than about 100 $\mu$M, about 10 $\mu$M, about 1 $\mu$M, about 0.1 $\mu$M, about 0.01 $\mu$M, about 0.001 $\mu$M or about 0.0001 $\mu$M. The administering step can be performed by any acceptable means, including oral, inhalation, topical, IV, IP, and IM administration. The mammal can generally be any mammal susceptible to asthma, preferably is a human, a cat, a dog, a cow, a horse, a pig, or a goat, and more preferably is a human. The plasminogen activator inhibitor-1 antagonist can generally be any plasminogen activator inhibitor-1 antagonist. Preferably, the plasminogen activator inhibitor-1 antagonist is an antibody, a protein, a peptide, a polynucleotide, or a small organic molecule. The antibody can be a monoclonal antibody or a polyclonal antibody. The plasminogen activator inhibitor-1 antagonist can be spironolactone, imidapril, an angiotensin converting enzyme inhibitor, captopril, enalapril, an angiotensin II receptor antagonist, or defibrotide.

An additional embodiment of the invention is directed towards the use of compounds which change the concentration of upstream regulators or downstream effector molecules of PAI-1, in treating or preventing asthma or chronic obstructive pulmonary disease. The method can comprise selecting a mammal diagnosed with asthma or chronic obstructive pulmonary disease, and administering to the mammal one or more compounds. The compounds can comprise urokinase, tissue plasminogen activator, vitronectin, plasminogen, plasmin, matrix metalloproteinases, or tissue inhibitors of metalloproteinases. The concentration of compound is preferably less than about 100 $\mu$M, about 10 $\mu$M, about 1 $\mu$M, about 0.1 $\mu$M, about 0.01 $\mu$M, about 0.001 $\mu$M or about 0.0001 $\mu$M. The administering step can be performed by any acceptable means, including oral, inhalation, topical, IV, IP, and IM administration. The mammal can generally be any mammal susceptible to asthma or chronic obstructive pulmonary disease, preferably is a human, a cat, a dog, a cow, a horse, a pig, or a goat, and more preferably is a human.

An additional embodiment of the invention is directed towards methods for the prevention of asthma and/or chronic obstructive pulmonary disease. The methods can comprise selecting a mammal, and administering to the mammal a plasminogen activator inhibitor-1 antagonist. The antagonist is preferably administered at a concentration suitable to reduce the occurrence or effects of asthma or chronic obstructive pulmonary disease relative to a mammal which did not receive the administration. The concentration of the antagonist is preferably less than about 100 $\mu$M, about 10 $\mu$M, about 1 $\mu$M, about 0.1 $\mu$M, about 0.01 $\mu$M, about 0.001 $\mu$M or about 0.0001 $\mu$M. The administering step can be performed by any acceptable means, including oral, inhalation, topical, IV, IP, and IM administration. The mammal can generally be any mammal susceptible to asthma or chronic obstructive pulmonary disease, preferably is a human, a cat, a dog, a cow, a horse, a pig, or a goat, and more preferably is a human. The plasminogen activator inhibitor-1 antagonist can generally be any plasminogen activator inhibitor-1 antagonist. Preferably, the plasminogen activator inhibitor-1 antagonist is an antibody, a protein, a peptide, a polynucleotide, or a small organic molecule. The antibody can be a monoclonal antibody or a polyclonal antibody. The plasminogen activator inhibitor-1 antagonist can be spironolactone, imidapril, an angiotensin converting enzyme inhibitor, captopril, enalapril, an angiotensin II receptor antagonist, or defibrotide.

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLES

Example 1

Sequences Relating to Allergic Inflammation

A DNA microarray (manufactured by Incyte/Systemix, Inc.) was used to analyze 7,000 sequences. To generate cDNA probes, a combination of PMA and A23187 was used for maximum stimulation of a human mast cell line, HMC-1 (from Butterfield, Mayo Clinic). Among more than 600 inducible sequences, PAI-1 mRNA was induced at the highest level (see Table 1). Numbers correspond to the degree of differential expression between resting and activated cells. Negative numbers represent upregulation after activation, while positive numbers represent downregulation after activation.

TABLE 1

| Differential expression | |
|---|---|
| Differential expression | Sequence name |
| −34.2 | Plasminogen activator inhibitor, type I |
| −4.2 | Plasminogen activator, urokinase receptor |
| −1.2 | Plasminogen activator, tissue-type (t-PA) |
| −1.1 | Plasminogen activator, urokinase-type (u-PA) |

Example 2

Blotting

Northern blot analysis was performed to confirm the results of the DNA microarray. Both 3.3 kb (alternative spliced mRNA) and 2.4 kb PAI-1 mRNA were induced in human mast cell line (HMC-1) cells at high level after treatment with PMA and A23187.

PAI-1 protein was measured by PAI-ELISA in HMC-1 cells and primary cultured human mast cells from cord blood to determine whether PAI-1 secretion is also enhanced in mast cells upon stimulation. PAI-1 secretion was enhanced in both HMC-1 cells and in primary cultured human mast cells after stimulation (see Table 2). Mast cells were cultured in umbilical cord blood, and were activated with IgE receptor. The PAI-1 concentrations represent mean values of four independent experiments performed in duplicate.

TABLE 2

| PAI-1 secretion | |
|---|---|
| Conditions | PAI-1 (ng/ml) |
| HMC- 1 resting | .5 |
| HMC-1 PMA/A activation | 170 |
| Mast cells resting | 2 |
| Mast cells IgE activation | 83 |

The kinetics of human PAI-1 message was examined by Northern blot analysis. The level of PAI-1 message increased at one hour after stimulation, began to decrease by six hours, and was comparable to resting state levels by 24 hours. The kinetics of PAI-1 message induction is similar to that of pro-inflammatory cytokines in mast cells.

Glucocorticoids are known to induce PAI-1 mRNA while cyclosporin suppresses transcription of gene expression. The effects of cyclosporin, dexamethasone, and cyclohexamide on PAI-1 expression in mast cells after stimulation was examined. Dexamethasone induced PAI-1 mRNA expression in a dose-dependent manner. Cyclosporin down regulated the expression of the PAI-1 gene. Cyclohexamide abrogated PAI-1 mRNA expression, suggesting that transcription of the PAI-1 gene requires de novo synthesis of early gene products, including transcription factors.

The expression of mRNA for murine PAI-1 in lung extracts of a murine asthma model was determined by semi-quantitative RT-PCR after the challenge to determine whether PAI-1 message is induced in asthmatic individuals. The PAI-1 message was induced eight hours after challenge. The presence of similar amounts of RNA for each condition was confirmed by demonstration of β-actin bands of similar intensity. The data support the hypothesis that induction of the murine PAI-1 gene occurs in asthmatic inflammation.

Example 3

Animals and Sensitization

Specific pathogen-free female FVB/NJ mice aged 8–10 weeks were obtained from Charles River (Wilmington, Mass.). Animals were maintained in a laminar flow holding unit (Gelman Sciences, Sydney) and housed in autoclaved cages on autoclaved bedding in an air-conditioned room on a 12 hour light/dark cycle. These 5 mice in a group were either sensitized by inhalational exposure to ovalbumin without prior systemic immunization or received an intraperitoneal injection of 10 μg of alum precipitated chicken egg ovalbumin (grade V, 98% pure, Sigma, St Louis, Mo.) 21 days before inhalational exposure and a booster injection seven days before inhalational exposure. Inhalational exposure was performed as described (Temelkovski, J., et al. Thorax. 53: 849, 1998; partially modified). All experimental procedures complied with the requirements of the Animal Care and Ethics Committee of the Harbor-UCLA Research Education Institute.

Example 4

Tissue Collection and Extraction of RNA from the Lung Tissue

For each time point sampled, tissues for histopathological examination were collected 24 hours after the last inhalational exposure. Animals were killed by exsanguination following an overdose of pentobarbital and the lung vasculature was perfused free of blood by slowly injecting 3 ml of PBS into the right ventricle. For histopathologic and immunofluorescence study, the trachea was then cannulated with a blunted #19 needle and the lungs were inflated with 10% buffered formalin. After fixation overnight, a horizontal slice from the mid zone of the single lobed left lung were embedded in paraffin. Ribbons of 2–3 sections cut at 5 μm were stained with Masson trichrome (for assessment of collagen deposition). To extract total RNA from the mice lung tissues, the extracted samples were rinsed in PBS three times and 100 mg of the specimen was homogenized in TRIzol reagent (Life Technologies, Gaithersburg, Md.). RNA extraction was performed according to the manufacturer's protocol.

Example 5

Reverse Transcription-polymerase Chain Reaction (RT-PCR)

The total RNA was reverse transcribed with avian myeloblastosis virus (AMV) reverse transcriptase (Invitrogen, Carlsbad, Calif.) at 37° C. for 1 hour using random hexamers in a total volume of 20 μl. Two μl of the cDNA was amplified with 0.2 mM dNTPs, and 2.5 units of Taq DNA polymerase in the buffer recommended by the supplier (Invitrogen). Amplification consisted of denaturation at 94° C. for 5 minutes followed by 28 cycles consisting of 94° C. for 1 minute, at 55° C. for 1 minute, and at 72° C. for 3 minutes; and was ended by a 10 minute extension at 72° C. The following primers were used: murine PAI-1 (504 bp); sense (5'-AGCAGAGTGGAGGGCACA-3'; SEQ ID NO:1) and antisense (5'-GATGCCGTATGCCACGGT-3'; SEQ ID NO:2). Amplification of fragments of the cDNA of glyceraldehyde-3-phosphate dehydrogenase (GAPDH) were performed in the same PCR reaction as the internal control with the following primers: murine GAPDH (239 bp); sense (5'-GAGTCTACTGGTGTCTTCACC-3'; SEQ ID NO:3) and antisense (5'-GTCATGAGCCCTTCCACAATGC-3'; SEQ ID NO:4). Half of each reaction mixture was analyzed by agarose gel electrophoresis. All experiments were performed three times with similar results. To verify the quantitation of the products, we performed RT-PCR repeatedly with serially diluted total RNA (1, 5, and 10 µg).

Example 6

Immunofluorescence Staining

The paraffin-embedded mice lung tissue was cut into 3µm sections. After the tissue was deparaffinized, nonspecific binding was blocked with 5% swine serum (Jackson Immunoresearch Laboratories Inc., West Grove, Pa.). After two washes with phosphate buffered saline (PBS), rabbit primary antibody against murine PAI-1 (1/100; Santa Cruz Biotechnology Inc., Santa Cruz, Calif.) was added and the section was incubated overnight at 4° C. Substitution of each primary antibody with normal rabbit serum (Jackson lmmunoresearch Laboratories Inc., West Grove, Pa.) at the same dilution was performed to control for non-specific binding. The sections were washed in PBS twice for 10 min each and then incubated for 1 hour at room temperature with the fluorescein-isothiocyanate (FITC)-labeled swine anti-rabbit antibody (1/20; Dako, Carpinteria, Calif.). After four washes in PBS for 10 minutes each, the coverslips were mounted and then examined using an Eclipse E400 microscope (Nikon Inc., Melville, N.Y.) equipped with epifluorescence optics.

Example 7

Bronchoalveolar Lavage and PAI-1 ELISA

The trachea was exposed and a 22 gauge angiocatheter was inserted and tied in place with a suture. The lungs were lavaged (three times) by slowly instilling 1 ml of sterile PBS at 37° C. followed by gentle aspiration. The BAL fluid was centrifuged (1,000×g for 10 minutes at 4° C.) to sediment the cells and the supernatants were removed and stored at −80° C. The total protein of the BAL supernatants were measured by Micro BSA protein assay reagent kit (Pierce, Rockford, Ill.). The BAL supernatants were assayed in duplicate for murine PAI-1 using sandwich ELISA (Molecular Innovations, Inc., Southfield, Mich.) following the manufacturer's directions. The lower limit of detection for these assays was 0.5 ng/ml. Results were expressed as ng/mg total protein.

Example 8

Characteristics of Patients

In order to investigate the potential contribution of the PAI-1 biallelic single nucleotide polymorphism to the risk of developing asthma, we studied siblings and parents from the Nottingham Asthma Family study. A total of 211 individuals from 51 families were genotyped. Families were identified on the basis of affected sib-pairs for asthma. Asthma was defined using a previously validated questionnaire together with a physician diagnosis of asthma. Atopy was defined as a positive skin prick test to one or more common allergens (Der pl, Fel dl, feathers). A positive response was considered to be 3 ml or greater than control.

Example 9

Genomic DNA Extraction

Blood was taken from each family member for Genomic DNA extraction, using QiAMP kit (Qiagen Inc., Valencia, Calif), as directed to obtain 3–12 µg of DNA from 200 µl whole blood.

Example 10

Determination of PAI-1 genotype

The PAI-1 4G/5G genotype was analyzed with an allele-specific PCR modified from Falk et al. (*Fibrinolysis* 9: 170, 1995), using an alternative forward primer (5'-GTCTGGACACGTGGGGG-3' (SEQ ID NO:5) for the 5G allele or 5'-GTCTGGACACGTGGGGA-3' (SEQ ID NO:6) for the 4G allele) with a common reverse primer (5'-GCTGTCCACCCGGTGCTCTG-3'; SEQ ID NO:7) (designed to minimize dimer-primer formation) and a control reverse upstream primer (5'-AAGCTTTTACCATGGTAACCCCTGGT-3'; SEQ ID NO:8). The PCR procedure included the hot-start initial step to avoid dimer-primer artifacts. The PCR mixture was subjected to 30 step cycles of 94° C. (1 minute), 60° C. (1 minute) and 72° C. (1 minute). Electrophoresis was performed in 2% agarose with 1× TAE buffer. A photograph was obtained after staining with ethidium bromide. Controls for this technique consisted of DNA samples of known genotype determined by DNA sequence analysis.

Example 11

Statistical Analysis

Statistical significance for the ELISA assay was determined by the Student's paired sample t test (two-tailed). P values <0.05 were considered to be significant. TDT of the 4G/5G polymorphism was performed using a sib-pair program to perform simple genetic analysis (SIB-PAIR version 0.99.3) (Duffy, D. *Am. Soc. Hum. Genet.* Suppl. 61: A197, 1997). The phenotypes studied were asthma and atopy.

Example 12

Determination of ECM Accumulation in a Murine Asthma Model

To determine the accumulation of collagen, which is an important component of ECM, Masson trichrome-staining was performed with the lung tissue of mice challenged for 4 weeks or 8 weeks. Extensive accumulation of collagen was showed in the lung tissue after challenge for 4 weeks or 8 weeks, whereas prechallenged control mice did not show significant collagen deposition in the lung.

Example 13

PAI-1 Gene Expression in a Murine Asthma Model

To determine whether the PAI-1 gene is induced in the lungs of the murine asthma model, semi-quantitative RT-PCR was performed with the lung extracts obtained before inhalation challenge and 4 weeks or 8 weeks after inhalation challenge. PAI-1 mRNA in the lung tissue was induced 4 weeks or 8 weeks after inhalation challenge by RT-PCR with 1, 5, or 10 µg of total RNA. PAI-1 mRNA in the lung tissue of the prechallenged control mice was found by RT-PCR with 10 µg of total RNA, but not with 1 µg or with 5 μg. The presence of similar amounts of RNA for each condition was confirmed by demonstration of GAPDH bands of similar intensity. These results indicate that PAI-1 mRNA is upregulated in murine asthma.

Example 14

Immunofluorescence Study of the Lung Tissue of a Murine Asthma Model

To determine whether the PAI-1 protein is also induced in lungs of a murine asthma model, the lung tissue was examined by indirect immunofluorescence study. The PAI-1 protein was localized predominantly to endothelial cells in mice before inhalation challenge. PAI-1 protein expression was more intense and widely distributed throughout the lung fields after inhalation challenge for four or eight week.

Example 15

PAI-1 Secretion in BAL Fluid from Murine Asthma Model

To determine whether the PAI-1 protein is secreted into the airways of a murine asthma model, the BAL fluid was examined. Supernatants from the BAL fluid were analyzed for the levels of murine PAI-1 protein. The PAI-1 levels were increased to 4.7 ±0.3 (p <0.001) and 7.0±1.1 (p <0.005) ng/mg protein four and eight weeks after inhalation challenge, respectively. The PAI-1 level from control mice was 0.9±0.2 ng/mg protein.

Example 16

4G/5G Genotype and Transmission Disequilibrium Test (TDT)

The distribution of the genotypes in the 102 children with asthma was determined as follows: 43 with 4G/4G (42.2%), 50 with 4G/5G (49.1%) and 9 with 5G/5G (8.8%). The prevalence of the 4G allele was similar overall in this population to the prevalence in previous reports (see Gene Bank report, Accession Number M91557). The results of the TDT between the 4G and 5G alleles in asthma and atopy in the families are shown in Table 3. The 4G allele was preferentially transmitted to asthma-affected children ($\chi^2$= 6.6, p =0.0139). There was a trend towards increased transmission of the 4G allele to atopic children (28 v 20 transmissions, Table 3) but this was not significant ($\chi^2$=1.3, p=0.3123). These results suggest that the 4G allele of the PAI-1 gene maybe associated with the development of asthma. The demonstration of increased transmission of the 4G allele in asthmatic siblings is in keeping with the observed functional effects of this allele in vitro, with increased levels of PAI-1 in the plasma of individuals carrying this allele due to increased transcriptional activity of the gene.

TABLE 3

| | Transmission disequilibrium test | | | |
| --- | --- | --- | --- | --- |
| | Transmitted | Not transmitted | TDT ($\chi^2$) | P-value |
| Asthma 4G | 44 | 23 | 6.6 | 0.0139 |
| Asthma 5G | 23 | 44 | | |
| Atopy 4G | 28 | 20 | 1.3 | 0.3123 |
| Atopy 5G | 20 | 28 | | |

Example 17

Characterization of PAI-1 as an Asthmatic Airway Remodeling Candidate

Human fetal asthma lung tissue was examined using double immunofluorescence co-localization of PAI-1 and tryptase in mast cells. PAI-1 was seen as yellow-red staining in airway smooth muscle. A tryptase positive but PAI-1 negative mast cell was shown for comparison. The results suggested that PAI-1 can be produced from tryptase positive mast cells in human asthmatic airways.

Parental mice (FVB/NJ, Charles River, Inc.) and PAI-1 knock-out mice (from Dr. Zlokovic, University of Southern California) were induced with ovalbumin for 8 weeks, with three times challenge weekly. Such challenges have produced infiltration of inflammatory cells, mucus accumulation, gross architectural changes, some smooth muscle hypertrophy, and collagen accumulation around the airway. The collagen accumulation is indicative of airway remodeling. These changes were not observed in the PAI-1 knock-out mice challenged for either four or eight weeks. This protective effect from airway remodeling is evidence of the role of PAI-1 for this disease indication.

Example 18

Production of Antibodies

Antibody antagonists to PAI-1 may be polyclonal antibodies or monoclonal antibodies. Any monoclonal antibody of this invention may be a chimeric or humanized antibody, a human antibody, or a DEIMMUNISED™ antibody. It might also consist of a whole antibody, a Fab, F(ab')$_2$, or single or double chain Fv fragment, a single chain antibody, or other form of antibody fragment. The antibody may be produced by any recombinant method known to the art and may be produced in vivo or in vitro.

Production of polyclonal antibodies

For polyclonal antibody production, denatured peptide from the reverse phase HPLC separation is obtained in quantities up to 75 mg. This denatured protein can be used to immunize mice or rabbits using standard protocols; about 100 micrograms are adequate for immunization of a mouse, while up to 1 mg might be used to immunize a rabbit. In identifying mouse hybridomas, the denatured protein can be labelled and used to screen potential murine B-cell hybridomas for those which produce antibody. This procedure requires only small quantities of protein, such that 20 mg would be sufficient for labelling and screening of several thousand clones.

Production of monoclonal antibodies

For monoclonal antibody production, the amino acid sequence of PAI-1 is analyzed to determine regions of high immunogenicity. Peptides comprising appropriate hydrophilic regions are expressed from recombinant cDNA or synthesized and used in suitable immunization protocols to raise antibodies. Selection of appropriate epitopes is described by Ausubel F. M. et al (Current Protocols in Molecular Biology, John Wiley & Sons, New York City, 1989). The optimal amino acid sequences for immunization are usually located at the C-terminus or N-terminus and in intervening, hydrophilic regions of the polypeptide which are likely to be exposed to the external environment when the protein is in its natural conformation.

Typically, selected oligopeptides, about 15 residues in length, are synthesized using an Applied Biosystems Peptide Synthesizer Model 431A using fmoc-chemistry and coupled to keyhole limpet hemocyanin (KLH, Sigma) by reaction with M-maleimidobenzoyl-N-hydroxysuccinimide ester (MBS; Ausubel F. M. et al, supra). If necessary, a cysteine may be introduced at the N-terminus of the peptide to permit coupling to KLH. Rabbits are immunized with the peptide-KLH complex in complete Freund's adjuvant. The resulting antisera are tested for antipeptide activity by binding the peptide to plastic, blocking with 1% bovine serum albumin, reacting with antisera, washing and reacting with labelled, affinity purified, specific goat anti-rabbit IgG.

Hybridomas may also be prepared and screened using standard techniques. Hybridomas of interest are detected by screening with labelled PAI-1 to identify those fusions producing the monoclonal antibody with the desired specificity. In a typical protocol, wells of plates (FAST; Becton-Dickinson, Palo Alto, Calif.) are coated during incubation with affinity purified, specific rabbit anti-mouse (or suitable anti-species Ig) antibodies at 10 mg/ml. The coated wells are blocked with 1% BSA, washed and incubated with supernatants from hybridomas. After washing the wells are incubated with labelled PAI-1 at 1 mg/ml. Supernatants with specific antibodies bind more labelled KIN than is detectable in the background. Then clones producing specific antibodies are expanded and subjected to two cycles of cloning at limiting dilution. Cloned hybridomas are injected into pristane-treated mice to produce ascites, and monoclonal antibody is purified from mouse ascitic fluid by affinity chromatography on Protein A. Monoclonal antibodies with affinities of at least $10^8$/M, preferably $10^9$ to $10^{10}$ or stronger, will typically be made by standard procedures as described in Harlow and Lane (1988) Antibodies: A Laboratory Manual, Cold Spring Harbor Laboratory, Cold Spring Harbor, N.Y.; and in Goding (1986) Monoclonal Antibodies: Principles and Practice, Academic Press, New York City, both incorporated herein by reference.

Production of Fab or $F(ab')_2$ antibody fragments

Generally, a preferred method for generating Fab antibody fragments comprises digestion of the selected antibody with papain and cysteine to generate IgG, Fab and Fc. A solution of the components is then loaded on a column containing Protein A. IgG and Fc to bind the column and Fab is present in the effluent. Similarly, a divalent $F(ab')_2$ fragment may be produced by digestion of the antibody with pepsin, followed by chromatographic separation.

Production of single chain antibodies

A method of the determination and construction of single chain antibodies ("ScFv") is described, for example, in U.S. Pat. No. 4,946,778 to Ladner, et al., incorporated herein by reference. Generally, such antibodies are produced by introducing into host cells a nucleic acid that encodes a single chain polypeptide with binding affinity for an antigen comprising the binding portion of the light chain variable region of an antibody, the binding portion of the heavy chain variable region of an antibody, and a polypeptide linker linking the light and heavy chain variable region binding portions into a single chain polypeptide having binding affinity for an antigen.

Chimeric and humanized antibodies

Chimeric antibodies are produced by recombinant processes well known in the art, and, generally, have an animal (e.g. murine) variable region and a human constant region. Humanized antibodies correspond more closely to the sequence of human antibodies than do chimeric antibodies. In a humanized antibody, only the complementarity determining regions (CDRs) which are responsible for antigen binding and specificity are animal-derived and have an amino acid sequence corresponding to the animal antibody, and substantially all of the remaining portions of the molecule (except, in some cases, small portions of the framework regions within the variable region) are human-derived and have a corresponding amino acid sequence to a human antibody. See L. Riechmann et al., Nature, 1988; 332: 323–327; U.S. Pat. No. 5,225,539 (Medical Research Council); U.S. Pat. Nos. 5,585,089; 5,693,761; 5,693,762; and 5,530,101 (Protein Design Labs, Inc.), incorporated herein by reference.

DELMMUNISED™ antibodies

DELMMUNISED™ antibodies are antibodies in which the potential T cell epitopes have been eliminated, as described in International Patent Application PCT/GB98/01473, incorporated herein by reference. Therefore, immunogenicity in humans is expected to be eliminated or substantially reduced when they are applied in vivo.

Human antibodies

Human antibodies can be made by several different methods, including by use of human immunoglobulin expression libraries (Stratagene Corp., La Jolla, Calif.; Cambridge Antibody Technology Ltd., London, England) to produce fragments of human antibodies ($V_H$, $V_L$, Fv, Fd, Fab, or $(Fab')_2$), and using these fragments to construct whole human antibodies by fusion of the appropriate portion thereto, using techniques similar to those for producing chimeric antibodies. Human antibodies can also be produced in transgenic mice with a human immunoglobulin genome. Such mice are available from Abgenix, Inc., Fremont, Calif., and Medarex, Inc., Annandale, N.J. In addition to connecting the heavy and light chain Fv regions to form a single chain peptide, Fab can be constructed and expressed by similar means (M. J. Evans et al., J. Immunol. Meth., 1995; 184: 123–138), incorporated by reference herein.

All of the wholly and partially human antibodies are less immunogenic to humans than wholly murine or animal-derived antibodies, as are the single chain antibodies. All these molecules are therefore less likely to evoke an immune or allergic response. Consequently, they are better suited for in vivo administration in humans than wholly animal antibodies, especially when repeated or long-term administration is necessary.

Example 19

Preparation of Chemically Conjugated Antibodies

Antibodies may be conjugated by linking the Fc region of one antibody to the Fc region of the second antibody. In a preferred embodiment, one antibody or antibody fragment is linked to the C-terminal end of the heavy chain of a second antibody or antibody fragment. Conjugation may be accomplished by conventional means of attaching other proteins to the C-terminal end of the heavy chain.

In a preferred embodiment, incubation of the two antibodies to be joined in a glutaraldehyde solution with Tris buffer should induce conjugate formation. See Current Protocols in Molecular Biology, John Wiley and Sons, Inc., 2000, pp. 11.1.4–11.1.5 and Short Protocols in Molecular Biology, 3rd ed., John Wiley and Sons, Inc., 1995, p. 11–4, incorporated by reference herein.

In another preferred embodiment, the antibodies or antibody fragments may be conjugated by first chemically or recombinantly modifying one antibody or antibody fragment to contain a carbohydrate side chain such as that present on and used for conjugation of horseradish peroxidase to antibodies. The antibody could then be conjugated to another antibody or antibody fragment using a protocol similar to that employed for horseradish peroxidase conjugation. See Current Protocols in Molecular Biology, John Wiley and Sons, Inc., 2000, pp. 11.1.1–11.1.3 and Short Protocols in Molecular Biology, 3rd ed., John Wiley and Sons, Inc., 1995, pp. 11-3–11-4, incorporated by reference herein.

Conjugated antibodies may also be produced by any recombinant methods known to the art. In such cases, the recombinant nucleic acid should encode at least the heavy and light chain variable region sequences responsible for binding to the antigen of both of the antibodies to be joined. The nucleic acid should additionally encode a product that is capable of binding to both of the antigens.

Example 20

Treatment of Asthma or Chronic Obstructive Pulmonary Disease

A patient suffering from asthma or chronic obstructive pulmonary disease can be treated with a formulation containing a PAI-1 antagonist. For example, an aqueous aerosol composition containing an antibody PAI-1 antagonist can be administered to a patient by means of an inhaler. The concentration of the antagonist is preferably less than about 100 $\mu$M, about 10 $\mu$M, about 1 $\mu$M, about 0.1 $\mu$M, about 0.01 $\mu$M, about 0.001 $\mu$M or about 0.0001 $\mu$M. The administering step can be performed by any acceptable means, including oral, inhalation, topical, IV, IP, and IM administration.

Alternatively, treatment or prevention of asthma or chronic obstructive pulmonary disease may be made with a formulation containing a molecule which down-regulates PAI-1 activity, including antibodies, antibody fragments, small molecule drugs including peptides, gene therapy, or physiological recombinant regulators of the protein that target or bind to PAI-1. Upstream regulators or downstream effector molecules of PAI-1, including urokinase, tissue plasminogen activator, vitronectin, plasminogen, plasmin, matrix metalloproteinases, or tissue inhibitors of metalloproteinases.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the methods described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention.

What is claimed is:

1. A method to treat asthma in a mammal, the method comprising:
   selecting a mammal diagnosed with asthma; and
   administering to the mammal a plasminogen activator inhibitor-1 antagonist wherein said plasminogen activator inhibitor-1 antagonist is an antibody.

2. The method of claim 1, wherein the mammal is a human, a cat, a dog, a cow, a horse, a pig, or a goat.

3. The method of claim 1, wherein the mammal is a human.

4. The method of claim 1, wherein the administering step comprises inhalation.

5. The method of claim 1, wherein the plasminogen activator inhibitor-1 antagonist is a polyclonal antibody.

6. The method of claim 1, wherein the plasminogen activator inhibitor-1 antagonist is a monoclonal antibody.

7. A method to treat chronic obstructive pulmonary disease in a mammal, the method comprising:
   selecting a mammal diagnosed with chronic obstructive pulmonary disease; and
   administering to the mammal a plasminogen activator inhibitor-1 antagonist wherein said plasminogen activator inhibitor-1 antagonist is an antibody.

8. The method of claim 7, wherein the mammal is a human, a cat, a dog, a cow, a horse, a pig, or a goat.

9. The method of claim 7, wherein the mammal is a human.

10. The method of claim 7, wherein the administering step comprises inhalation.

11. The method of claim 7, wherein the plasminogen activator inhibitor-1 antagonist is a polyclonal antibody.

12. The method of claim 7, wherein the plasminogen activator inhibitor-1 antagonist is a monoclonal antibody.

* * * * *